United States Patent [19]
Sebillotte-Arnaud et al.

[11] Patent Number: 6,136,328
[45] Date of Patent: *Oct. 24, 2000

[54] O/W EMULSION WITH A HIGH ELECTROLYTE CONTENT AND ITS USE IN DERMOCOSMETICS, IN PARTICULAR FOR TREATING IRRITATION AND/OR SENSITIVE SKIN PHENOMENA

[75] Inventors: Laurence Sebillotte-Arnaud, L'Hay les Roses, France; Didier Gagnebien, Westfield, N.J.

[73] Assignee: L'Oreal, Paris, France

[*] Notice: This patent issued on a continued prosecution application filed under 37 CFR 1.53(d), and is subject to the twenty year patent term provisions of 35 U.S.C. 154(a)(2).

[21] Appl. No.: 08/949,685

[22] Filed: Oct. 14, 1997

[30] Foreign Application Priority Data

Oct. 11, 1996 [FR] France ..................... 96 12450

[51] Int. Cl.$^7$ ....................................... A61K 7/02
[52] U.S. Cl. ............................... 424/401; 424/63
[58] Field of Search ....................... 424/401, 63

[56] References Cited

U.S. PATENT DOCUMENTS

| | | | |
|---|---|---|---|
| 4,285,973 | 8/1981 | Edwards | 424/358 |
| 4,606,913 | 8/1986 | Aronson et al. | 424/59 |
| 4,743,442 | 5/1988 | Raaf et al. | 424/47 |
| 5,589,178 | 12/1996 | Aubert | 424/401 |

FOREIGN PATENT DOCUMENTS 0 530 531   3/1993   European Pat. Off. .

OTHER PUBLICATIONS

S. Kobayashi, Chemical Abstracts, Abstract No. 141260, Apr. 17, 1989, vol. 110, No. 16.

*Primary Examiner*—Richard L. Raymond
*Attorney, Agent, or Firm*—Oblon, Spivak, McClelland, Maier & Neustadt, P.C.

[57] ABSTRACT

A composition in the form of an O/W emulsion comprising at least 2% by weight, relative to the total weight of the composition, of at least one water-soluble metal salt, and from 2–4.5% by weight, relative to the total weight of the composition, of a suitable emulsifying system, excluding compositions comprising 1% by weight of a gelling agent consisting of a combination of a polyacrylamide, $C_{13}$–$C_{14}$ isoparaffin and laureth-7 (CTFA).

23 Claims, No Drawings

O/W EMULSION WITH A HIGH ELECTROLYTE CONTENT AND ITS USE IN DERMOCOSMETICS, IN PARTICULAR FOR TREATING IRRITATION AND/OR SENSITIVE SKIN PHENOMENA

BACKGROUND OF THE INVENTION

1. Field of the Invention

The present invention relates to a stable oil-in-water emulsion with a high electrolyte content, comprising at least 2% by weight, relative to the total weight of the composition, of a water-soluble metal salt, and a suitable emulsifying system in an amount which is sufficient to obtain a stable composition which is useful in particular for topical application. More particularly, the invention relates to the use of the composition of the invention in dermocosmetics, in particular for pathological and/or physiological disorders associated with the release of substance P and/or of TNF-alpha (Tumor Necrosis Factor-alpha) and in particular for treating sensitive skin, skin disorders and diseases on which pruritus, rosacea and/or discreet erythema is present.

2. Description of the Background

It is known that certain skins are more sensitive than others. The symptoms of sensitive skins have hitherto been poorly characterized and the problems of such skins has, consequently, been poorly defined, since no-one has known the exact nature of the process involved in skin sensitivity-non-allergic hyperreactivity of the skin. Some have thought that a sensitive skin is a skin which reacts to cosmetic and/or dermatological products, while others have thought that sensitivity involved skin which reacts to several external factors, which are not necessarily associated with cosmetic and/or dermatological products.

Certain tests have been tried in an attempt to delimit sensitive skins, for example tests with lactic acid and with DMSO which are known to be irritant substances, see, for example, the article by K. Lammintausta et al, Dermatoses, 1988, 36, pages 45–49, and the article by T. Agner and J. Serup, Clinical and Experimental Dermatology, 1989, 14, pages 214–217. However, these tests have not made it possible to characterize sensitive skins, which have been likened to allergic skins.

The symptoms associated with sensitive skins have been revealed and described in patent application FR 95/04268 filed Apr. 10, 1995 in the name of L'Oreal. These symptoms are, in particular, subjective signs which are essentially dysaesthesic sensations. The term dysaesthesic sensations is understood to refer to the more or less painful sensations experienced in a region of skin, such as stinging, tingling, itching or pruritus, burning, heating, discomfort, tightness, etc.

It has also been shown that a sensitive skin is not an allergic skin, since an allergic skin is a skin which reacts to an external agent, an allergen, thereby triggering an allergic reaction. This is an immunological process which takes place only when an allergen is present, and which only affects the sensitized individuals. The essential characteristic of sensitive skin is, in contrast, a mechanism of response to external factors, which may concern any individual, even though individuals with so-called sensitive skin react faster thereto than other people. This mechanism is a specific rather than immunological.

Sensitive skins may be divided into two major clinical forms, irritable skins and intolerant skins. An irritable skin is a skin which reacts by pruritus, that is to say by itching or by stinging to various factors such as the environment, the emotions, foods, the wind, friction, shaving, hard water with a high calcium concentration, temperature variations or wool. In general, these signs are associated with a dry skin with or without dry patches, or with a skin which exhibits erythema. An intolerant skin is a skin which reacts by heating, tightness or tingling sensations and/or redness, to various factors such as the application of cosmetic or dermatological products or soap. In general, these signs are associated with an erythema and with a hyperseborrhoeic or acneic, or even rosaceiform, skin, with or without dartres.

In general, sensitive skins are defined by a particular skin reactivity. This hyperreactivity may especially be brought into play by environmental, emotional or food factors or alternatively by the application of or contact with cosmetic or dermatological products. This hyperreactive state which defines sensitive skins differs from that of the ubiquitous reactivity brought about by irritants which induce irritation of the skin in almost all people.

This hyperreactive state is experienced and recognized by people suffering from it as "sensitive skin". "Sensitive" scalps have a more univocal clinical semeiology, that is, the sensations of pruritus and/or of stinging and/or of heating are essentially triggered by local factors such as friction, soap, surfactants, hard water with a high calcium concentration, shampoos or lotions. These sensations are also occasionally triggered by factors such as the environment, the emotions and/or foods. An erythema and hyperseborrhoea of the scalp, along with a state in which dandruff is present, are often associated with the above signs.

Moreover, in certain anatomical regions such as the major folds (inguinal, genital, axillary, popliteal, anal and submammary regions and in the crook of the elbow) and the feet, sensitive skin is reflected by pruriginous sensations and/or dyeaesthesic sensations (heating, stinging) associated in particular with sweat, friction, wool, surfactants, hard water with a high calcium concentration and/or temperature variations.

Pruritus is a common symptom of dermatitis, which often causes appreciable inconvenience for the patient when the pruritus is very severe, and the inconvenience may be such that the patient cannot continue his or her usual activity. In addition, the pruritus may be a source of excoriation complications which may become overinfected, lichenification of the pruriginous zones, the consequence of which is to place the patient in a veritable vicious circle. Among the dermatitides commonly associated with pruritus, mention may be made of eczema, atopical dermatitis, contact dermatitis, flat lichens, prurigo, urticaria, pruriginous toxidermia and certain clinical forms of psoriasis.

Pruritus is occasionally the predominant pathological sign on the skin, as in the cases of aquagenic pruritus, pruritus of the scalp during bouts of dandruff (pityriasis capitis), the pruritus of blood dialysis patients, renal insufficiency patients, AIDS patients and people suffering from biliary obstructions, or alternatively of pruritus in the paraneoplastic manifestations of certain cancers.

Furthermore, pruritus is a sign often encountered during certain skin or general parasitic attacks. These may be, for example, scabies, filariasis, oxyuriasis or cutaneous demodecidosis.

Since the characteristics of sensitive skins have been poorly understood, it has hitherto been very difficult to treat them. They have been treated indirectly, for example by limiting, in cosmetic or dermatological compositions, the use of products with an irritant nature such as surfactants, preserving agents or fragrances, as well as certain active agents.

Hitherto, pruritus have been treated using emollient preparations, local corticoids, PUVA-therapy or antihistamines. Local corticoids are, admittedly, very effective at soothing the symptoms but, unfortunately, their effect is not immediate. Furthermore, they have side effects that are often very penalizing, such as atrophy, and they expose the user to risks of mycosal and/or bacterial infections. PUVA-therapy is local irradiation of diseased skin with UVA rays, after absorption of a photosensitizing substance (psoralene). This technique has the serious drawbacks of photo-ageing which may lead to skin cancer. Furthermore, this treatment is not ambulatory, thus obliging sufferers to go regularly to a specialized center throughout the duration of the treatment, which is very restricting and limits their professional activity. Emollients have a very modest antipruriginous effect and are of poor efficacy when there is considerable pruritus. Moreover, antihistamines are not of constant efficacy and need to be taken orally.

There is thus a need for a treatment of these skin complaints which does not have these drawbacks.

The use of at least one metal salt, in particular a salt of an alkaline earth metal, which makes it possible to effectively treat pruritus or "sensitive skin" problems while at the same time overcoming the drawbacks mentioned above has been described in patent application FR 95/04268 filed on Apr. 10, 1995 in the name of L'Oreal.

Gelled compositions with a high electrolyte content are described in patent applications FR 96/00742 and FR 96/03094 filed on Jan. 27, 1996 and on Mar. 12, 1996 in the name of L'Oreal.

The present invention relates to a novel oil-in-water (O/W) emulsion composition comprising a high content of metal salts, which makes it possible in particular to treat the problems of "sensitive skin", especially pruritus. The composition of the invention is preferably a cosmetic or dermatological composition.

In the cosmetic field, it is common to use creams consisting of an O/W emulsion containing an oily phase dispersed in an aqueous phase. These emulsions often have problems of stability which make them difficult to manufacture. Thus, various means have been envisaged for overcoming this drawback. One means of overcoming it consists in strongly increasing the emulsifier content of these emulsions. However, it is known that emulsifiers used in large amount may prove to be irritant towards certain types of skin. It will be readily appreciated that such compositions are not suitable for application to sensitive skins in view of the problems outlined above.

Various O/W emulsion compositions with a high electrolyte content are described in the prior art. Thus, patent application EP 530,531 (Benckiser) describes a cosmetic composition in the form of an O/W or W/O emulsion comprising an emulsifying system and at least 2% (preferably at least 5%) of a water-soluble salt of alkali metals or of alkaline-earth metals. The salt is preferably a magnesium salt which acts as preserving agent. The subject of this application makes it possible to obtain cosmetic compositions free of preserving agents. For the O/W emulsions, the compositions comprise from 5–10% by weight of emulsifying system, generally 8% by weight.

It is important to have available a stable O/W emulsion composition containing a high electrolyte content which is suitable for topical application, in particular for treating the problems of sensitive skin and pruritus.

The present invention thus relates to a novel composition in the form of an O/W emulsion, comprising at least 2% by weight, preferably at least 3% by weight and more preferably at least 5% by weight, relative to the total weight of the composition, of at least one water-soluble metal salt, and from 2–4.5% by weight, preferably from 2–4% by weight, relative to the total weight of the composition, of a suitable emulsifying system, with the exception of compositions comprising 1% by weight of a gelling agent consisting of the combination of a polyacrylamide, $C_{13}$–$C_{14}$ isoparaffin and laureth-7 (CTFA) (marketed under the name Sepigel 305 by the company SEPPIC).

According to the present invention, the term metal salt is understood to refer to a salt of a metal of a simple substance which is capable of releasing simple cations (Dictionnaire de la Chimie et de ses Applications, Duval & Duval, 3rd edition, 1978, Technique and Documentation).

The water-soluble metal salts are more particularly chosen from the water-soluble salts of alkali metals or of alkaline-earth metals, of transition metals and of metals from Groups 13 and 14 of the Periodic Table of the Elements.

Suitable water-soluble salts of alkali metals which are useful of the invention include lithium, sodium and potassium salts.

Suitable water-soluble salts of alkaline earth metals which are useful in the invention include beryllium, magnesium, calcium, strontium and/or barium salts.

Suitable water-soluble salts of transition metals which are useful in the invention include the lanthanide salts and salts of the metals in the fourth period of the Periodic Table of the Elements, such as magnesium, cobalt and zinc salts.

Suitable water-soluble salts of metals from Groups 13 and 14 of the Periodic Table of the Elements which are useful in the invention include aluminum and tin salts.

The term lanthanide is understood to refer to the elements of atomic number z ranging from 57–71, which are lanthanum, cerium, praseodymium, neodymium, promethium, samarium, europium, gadolinium, terbium, dysprosium, holmium, erbium, thulium, ytterbium and lutetium.

The water-soluble metal salts of the invention are preferably chosen from the lithium, strontium, barium, yttrium, neodymium, gadolinium, manganese and zinc salts, more preferably the strontium salts.

These salts may be, for example, carbonates, bicarbonates, sulfates, glycerophosphates, berates, chlorides, nitrates, acetates, hydroxides or persulphates, as well as α-hydroxy acid salts or salts of fruit acids (citrate, tartrate, lactate, malate), or alternatively salts of amino acids (aspartate, arginate, glucocholate, fumarate) or salts of fatty acids (palpitate, oleate, caseinate, behenate).

The salt is preferably selected from the nitrates and chlorides, in particular, of lithium, strontium, barium, yttrium, neodymium, gadolinium, manganese and zinc, the sulfates of calcium, strontium and magnesium and the acetates of strontium or magnesium.

The amount of water-soluble metal salts in the composition of the invention is advantageously between 2% and 20% by weight relative to the total weight of the composition, preferably between 5% and 10% by weight.

The expression suitable emulsifying system is understood to refer to any emulsifier or mixture of emulsifiers which can produce a stable O/W emulsion with a high electrolyte content when they are present in the composition at a content of between 2 and 4.5% by weight relative to the total weight of the composition.

According to the invention, the expression stable O/W emulsion is preferably understood to refer to an emulsion which remains stable for at least 1 month at 45° C.

The suitable emulsifying system advantageously consists of at least one fatty acid ester of polyethylene glycol (PEG) and/or of at least one fatty acid ester of a polyoxyethylenated polyol, which are suitable for the preparation of O/W emulsions. The emulsifying system may also comprise at least one fatty acid ester of a polyol.

The suitable emulsifying system preferably consists of at least one fatty acid ester of PEG and at least one fatty acid ester of a polyol.

According to the invention, the term fatty acid is preferably understood to refer to linear or branched, saturated or unsaturated aliphatic acids comprising at least 10 carbon atoms, preferably between 10 and 20 carbon atoms, more preferably between 12 and 18 carbon atoms. These are, more particularly, lauric acid, palmitic acid, stearic acid, isostearic acid and oleic acid.

According to the invention, the expression fatty acid ester of PEG is preferably understood to refer to the esters of the fatty acids as defined above and of PEG comprising n PEG units, n being an integer at least equal to 8, preferably between 10 and 100, more preferably between 20 and 100. Preferred fatty acid esters of PEG of the invention are PEG-n stearates, n being an integer between 8 and 100, which are marketed under the name Myrj by the company ICI, more preferably PEG-20 stearate or PEG-40 stearate, marketed under the name Myrj 49 and Myrj 52 by the company ICI.

Among the polyoxyethylenated fatty acid esters of a polyol (n-OE, n is an integer greater than or equal to 2:OE represents the oxyethylene unit), mention may be made in particular of oxyethylenated sorbitan tristearate (20-OE), oxyethylenated sorbitan trioleate (20 OE), oxyethylenated sorbitan monolaurate (5-OE), oxyethylenated sorbitan monostearate (20-OE), oxyethylenated sorbitan monopalmitate (20-OE) and oxyethylenated sorbitan monooleate (20-OE).

According to the invention, the expression fatty acid ester of a polyol is preferably understood to refer to the mono- or polyesters of the fatty acids as defined above and of polyols, while the term polyols is preferably understood to refer to $C_3$–$C_6$ polyhydric alcohols comprising 3–6 hydroxyls. These are, more particularly, sugars and glycerol.

The sugars are advantageously selected from $C_5$–$C_6$ sugars of natural or synthetic origin, more particularly sorbitol. The fatty acid esters of a sugar are preferably selected from the fatty acid mono- or triesters of sorbitol, in particular those marketed under the names Arlacel or Span by the company ICI. In particularly advantageous manner, the fatty acid ester of a sugar is sorbitol tristearate, marketed in particular under the name Span 65 by the company ICI.

Among the fatty acid esters of glycerol, mention may be made of the fatty acid mono- or diesters of glycerol, in particular glyceryl mono- or distearate, and mixtures thereof in all proportions.

Preferably, the fatty acid ester of PEG/fatty acid ester of a polyol weight ratio is between 0.2 and 3, preferably between 0.25 and 2.5.

According to a first embodiment of the invention, the suitable emulsifying system consists of the combination of PEG-40 stearate and sorbitol tristearate, the PEG stearate/ sorbitol tristearate weight ratio ranging from 0.2–3, preferably from 0.25–2.

According to a second embodiment of the invention, the emulsifying system consists of the combination of PEG-20 stearate and of a mixture of PEG-100 stearate and glycerol mono/distearate (marketed in particular under the name Arlacel 165 by the company ICI), the PEG-20 stearate/ mixture weight ratio being between 0.2 and 3, preferably between 0.25 and 1.5.

The emulsifying system preferably has an HLB of greater than or equal to 9, advantageously greater than or equal to 11. Preferably, the emulsifying system has an HLB balance of less than or equal to 18. The HLB (hydrophilic-lipophilic balance) of an emulsifier is calculated according to the following formula:

$$HLB = \frac{100 - l}{5}$$

wherein L represents the weight percentage of the lipophilic group relative to the weight of the whole molecule. When several emulsifiers are present in the emulsifying system, the HLB of the emulsifying system corresponds to the average HLB calculated as a function of the amount of emulsifiers present.

The aqueous phase of the emulsion of the invention may comprise water, purified water, a flower water such as cornflower water, or a natural thermal or mineral water and mixtures thereof. For example, the natural thermal or mineral water may be selected from eau de Vittel, waters from the Vichy basin, eau d'Uriage, eau de la Roche Posay, eau de la Bourboule, eau d'Enghien-les-Bains, eau de Saint Gervais-les-Bains, eau de Neris-les-Bains, eau d'Allevard-les-Bains, eau de Digne, eau de Maizieres, eau de Neyrac-les-Bains, eau de Lons-le-Saunier, les Eaux Bonnes, eau de Rochefort, eau de Saint Christau, eau des Fumades, eau de Tercis-les-bains, eau d'Avene or eau d'Aix-les-Bains.

The aqueous phase preferably consists of a thermal water known for its soothing, anti-irritant and anti-radical properties when applied to the skin, in particular eau de la Roche Posay. Such thermal waters generally have a high electrolyte content, in particular comprising water-soluble salts of alkaline-earth metals, obviously, the amount of alkaline earth metals in the thermal water will be taken into account in order to determine the total amount of alkaline earth metals in the composition of the invention.

The aqueous phase may be present in an amount ranging from 30–80% by weight relative to the total weight of the composition, preferably from 40–70% by weight.

The fatty phase of the emulsion of the invention may comprise fatty substances commonly used in the field of application envisaged. Suitable fatty substances include silicone fatty substances such as silicone oils, as well as non-silicone fatty substances such as plant, mineral, animal and synthetic oils.

Silicone fatty substances include:
  (i) poly($C_1$–$C_{20}$)alkylsiloxanes and in particular those containing trimethylsilyl terminal groups, among which are linear polydimethylsiloxanes (PDMS) and alkylmethylpolysiloxanes such as cetyldimethicone (CTFA name).
  (ii) volatile silicone oils such as:
    cyclic volatile silicones having from 3–8 and preferably from 4–6 silicon atoms. These are, for example, cyclotetradimethylsiloxane, cyclopentadimethylsiloxane and cyclohexadimethylsiloxane.

linear volatile silicones having from 2–9 silicon atoms. These are, for example, hexamethyldisiloxane, hexyl heptamethyltrisiloxane and octyl heptamethyltrisiloxane.

Non-silicone fatty substances include common oils such as liquid paraffin, liquid petroleum jelly, almond oil, perhydrosqualene, apricot oil, wheat germ oil, sweet almond oil, beauty-leaf oil, palm oil, castor oil, avocado oil, jojoba oil, olive oil or cereal germ oil; esters of fatty acids or of fatty alcohols, such as octyldodecyl myristate or benzoates of $C_{12}$–$C_{15}$ alkyl alcohols; acetylglycerides; octanoates, decanoates or ricinoleates of alcohols or of polyalcohols; hydrogenated polyisobutene, hydrogenated oils that are solid at 25° C.; lanolins; fatty acids that are solid at 25° C.

These fatty substances may be selected in particular in a varied manner by those skilled in the art in order to prepare a composition having the desired properties, for example the desired consistency or texture properties.

Thus, the fatty phase of the emulsion of the invention may be present in an amount ranging from 20–70% by weight relative to the total weight of the composition, and preferably from 20–50% by weight.

In addition, the composition of the invention may comprise at least one stabilizer which is suitable for an O/W emulsion with a high electrolyte content. Such stabilizers are selected in particular from $C_0$–$C_{20}$ fatty alcohols or fatty acids, and water-soluble gelling agents such as xanthan gum, carob gum, guar gum, carrageenans or gellane.

The amount of stabilizer advantageously ranges from 0–10% by weight relative to the total weight of the composition, preferably between 0.1 and 5% by weight.

The compositions of the invention can be advantageously prepared as a cream, a milk, or the like.

In a known manner, the emulsion of the invention may also contain adjuvants that are common in the cosmetic and/or dermatological fields which include preserving agents, antioxidants, complexing agents, solvents, fragrances, fillers (for example a matt-effect agent), screening agents, bactericides, odor absorbers, dyestuffs, and the like. The amounts of these various adjuvants are those used conventionally in the field considered, and, for example, from 0.01–5% by weight relative to the total weight of the composition. Depending on their nature, these adjuvants may be introduced into the fatty phase or into the aqueous phase.

The present composition may also comprise at least one active compound which can induce skin irritation.

The present composition may also be used to reduce the irritant effect of at least one active compound administered separately in a cosmetic or pharmaceutical composition, topically (cream, lotion, gel, etc.) or systemically (orally, rectally, parenterally, etc.). The present composition may be applied to the skin simultaneously with the administration of the active agent liable to cause irritation, or it may be applied separately in time.

Proteins or protein hydrolyeates, amino acids, polyols, urea, allantoin, sugars and sugar derivatives, water-soluble vitamins, starch and bacterial or plant extracts, in particular Aloe vera extracts, may be used as hydrophilic active agents.

Retinal (vitamin A) and its derivatives, tocopherol (vitamin E) and its derivatives, essential fatty acids, ceramides and essential oils may be used as lipophilic active agents.

These active agents may be intended in particular to prevent and/or treat skin complaints. These active agents include, for example:

agents which modify skin differentiation and/or proliferation and/or pigmentation, such as retinoic acid and its isomers, retinol and its esters, retinoids, in particular those described in patent applications FR 2,570,377, EP 199,636, EP 325,540 and EP 402,072, retinal, vitamin D and its derivatives, oestrogens such as oestradiol, kojic acid or hydroquinone;

antibacterial agents such as clindamycin phosphate, erythromycin or antibiotics of the tetracycline class;

antiparasitic agents, in particular metronidazole, crotamiton or pyrethroids;

antifungal agents, in particular compounds belonging to the imidazole class, such as econazole, ketoconazole or miconazole or their salts, polyene compounds such as amphotericin B, compounds of the allylamine family such as terbinafine, or alternatively octopirox;

steroidal anti-inflammatory agents such as hydrocortisone, betamethasone valerate or clobetasol propionate, or non-steroidal anti-inflammatory agents such as ibuprofen and its salts, diclofenac and its salts, acetylsalicylic acid, acetaminophen or glycyrrhetinic acid;

anaesthetics such as lidocaine hydrochloride and its derivatives;

antipruriginous agents such as thenaldine, trimeprazine or cyproheptadine;

antiviral agents such as acyclovir;

keratolytic agents such as alpha- and beta-hydroxyearboxylic acids or beta-ketocarboxylic acids, their salts, amides or esters and more particularly alpha-hydroxy acids such as glycolic acid, lactic acid, tartaric acid, malic acid, citric acid, mandelic acid and, in general, fruit acids and beta-hydroxy acids such as salicylic acid and its derivatives, in particular alkylated derivatives such as 5-n-octanoylsalicylic acid;

anti-free radical agents such as α-tocopherol or its esters, superoxide dismutases, certain metal-chelating agents or ascorbic acid and its esters;

antiseborrhoeic agents such as progesterone;

antidandruff agents such as octopirox or zinc pyrithione;

antiacne agents such as retinoic acid or benzoyl peroxide;

antimetabolites;

agents to combat hair loss such as minoxidil;

antiseptic agents.

The present composition may also comprise as active agent at least one keratolytic agent and/or at least one neuropeptide antagonist and/or at least one inflammation-mediator antagonist, which are different from water-soluble metal salts, in particular for treating sensitive skin.

Keratolytic agents which are useful of the invention include alpha- and beta-hydroxycarboxylic acids or beta-ketocarboxylic ketocarboxylic acids, their salts, amides or esters and more particularly alpha-hydroxy acids such as glycolic acid, latic acid, tartaric acid, malic acid, citric acid, mandelic acid and, in general, fruit acids and beta-hydroxy acids such as salicylic derivatives, in particular alkylated as 5-n-octanoylsalicylic acid. These keratolytic agents may advantageously be present in the composition of the invention in amounts up to 10% by weight relative to the total weight of the composition, preferably between 0.1 and 5% by weight.

Suitable neuropeptide antagonists which are useful in the invention include P antagonists and CGRP antagonists and, and inflammationmediator antagonists include histamine, of interleukin-1 or of TNF-α. These antagonists may be present in a proportion of from 0.000001–10% by weight relative to the total weight of the composition and preferably from 0.0001–5%.

Advantageously, receptor-antagonists of substance P of CGRP and/or of interleukin-1 are preferably used.

Substance P antagonists which are useful of the invention include substances of organic or inorganic origin which are capable of producing an inhibition of the binding of substance P to the receptor or an inhibition of the synthesis and/or release of substance P by sensitive nerve fibres.

Substance P receptor antagonists in particular include a peptide or a non-peptide derivative containing a hetero atom, and more precisely a compound containing a heterocycle or a hetero atom linked directly or indirectly to a benzene ring.

Sendide and Spantide II may be used, for example, as substance P receptor-antagonist peptides.

The peptides described in the patents and patent applications U.S. Pat. No. 4,472,305, U.S. Pat. No. 4,839,465, EP 101,929, EP 333,174, EP 336,230, EP 394, 989, EP 44,332, EP 498,069, EP 515,681, EP 517,589, WO 92/22569 and GB 2,216,529 may also be used in the invention as peptides.

The non-peptide substance P receptor antagonists which are useful in the invention are, in particular, heterocyclic compounds, in particular sulfur-containing, nitrogen-containing or oxygen-containing compounds or compounds comprising a nitrogen atom linked directly or indirectly to a benzene ring.

The heterocyclic compounds described in the following patent applications include EP 360,390, EP 429,366, EP 430,771, EP 499,313, EP 514,273, EP 514,274, EP 514,275, EP 514,276, EP 520,555, EP 528,495, EP 532,456, EP 545,478, EP 558,156, WO 90/05525, WO 90/05729, WO 91/18878, WO 91/18899, WO 92/12151, WO 92/15585, WO 92/17449, WO 92/20676, WO 93/00330, WO 93/00331, WO 93/01159, WO 93/01169, WO 93/01170, WO 93/06099, WO 93/09116 and WO 94/08997 may be used in the invention as heterocyclic compounds. In particular, a compound comprising at least one nitrogen-containing heterocycle is a 2-tricyclyl-2-aminoethane derivative, a spirolactam derivative, a quinuclidine derivative, an azacyclic derivative, an aminopyrrolidine derivative, a piperidine derivative, an aminoazaheterocycle or an isoindole derivative.

As compounds containing a nitrogen atom linked directly or indirectly to a benzene ring, mention may be made of those described in patent applications EP 522,808 and WO 93/01165.

Suitable CGRP antagonists which are useful in the invention include any substance of organic or inorganic origin which is capable of inhibiting the binding of CGRP to the receptor or of inhibiting the synthesis and/or release of CGRP by sensitive nerve fibres.

For a substance to be recognized as a CGRP antagonist, it must in particular have a CGRP-antagonist pharmacological activity, that is to say of inducing a coherent pharmacological response in particular in one of the following tests:

the antagonist substance must reduce the vasodilation induced by capsaicin and/or the antagonist substance must induce an inhibition of the release of CGRP by sensitive nerve fibres and/or the antagonist substance must reduce an inhibition of the contraction of the smooth muscle in the vas deferens induced by CGRP.

In addition, the CGRP antagonist must have an affinity for the CGRP receptors.

CGRP 8–37, which is an anti-CGRP antibody, may be used in the invention, for example, as CGRP receptor antagonist.

When the composition of the invention comprises an active compound which can induce a skin irritation, selected from keratolytic agents, neuropeptide antagonists and inflammation-mediator antagonists, other than water-soluble metal salts, the amount of emulsifying system will be suitable to obtain a stable composition, according to the stability criteria defined above. Here also, it is preferred to use the minimum amount of emulsifying system which makes it possible to obtain a stable composition. A suitable amount of emulsifying system is thus an amount which is necessary and sufficient to obtain a stable composition for at least one month at 45° C. Such an amount is preferably less than 10% by weight relative to the total weight of the composition, more preferably less than 8% by weight.

Having now generally described the invention, a further understanding can be obtained by reference to certain specific examples, which are provided herein for purposes of illustration only and are not intended to be limiting unless otherwise specified.

The amounts herein are given as a percent (%) by weight relative to the total weight of the composition.

EXAMPLE 1

O/W cream

| Ingredients | | % |
|---|---|---|
| A: Fatty phase: | | |
| Mixture of PEG-100 stearate and glyceryl mono/distearate (marketed in particular under the name Arlacel 165 by the company ICI) | | 1.2 |
| PEG-20 stearate (marketed under the name Myrj 49 by the company ICI) | | 1.2 |
| Stearic acid | | 0.6 |
| Cetyl alcohol | | 0.6 |
| Stearyl alcohol | | 0.6 |
| Cyclomethicone | | 7.0 |
| Fatty ester | | 19.0 |
| Plant oil | | 4.0 |
| B: Aqueous phase: | | |
| Glycerol | | 3.0 |
| Preserving agents | qs | |
| Strontium chloride.6H$_2$O | | 5.5 |
| Distilled water | qs | 100 |
| C: Annex phase: | | |
| Xanthan gum | | 0.2 |
| Distilled water | | 10.0 |

The O/W cream is prepared according to the following procedure:

phases A and B are heated to 75° C. separately and phase A is then poured gradually into phase B at 600 rpm;

the mixture is allowed to cool to 40° C. with stirring at 600 rpm;

phase C is then added at 1500 rpm, after which the emulsion is stirred at 3000 rpm for 5 min.

An emulsion which is stable for at least 1 month at 45° C. is obtained.

EXAMPLE 2

O/W cream

| Ingredients | | % |
|---|---|---|
| A: Fatty phase: | | |
| Sorbitol tristearate | | 0.9 |
| (marketed under the name | | |
| Span 65 by the company ICI) | | |
| PEG-40 stearate | | 2.0 |
| (marketed under the name | | |
| Myrj 52 by the company ICI) | | |
| Cetyl alcohol | | 4.0 |
| Glyceryl stearate | | 3.0 |
| Cyclomethicone | | 10.0 |
| Hydrogenated isoparaffin | | 14.0 |
| (6–8 mol of isobutylene) | | |
| B: Aqueous phase: | | |
| Preserving agents | qs | |
| Strontium chloride.6H$_2$O | | 6.6 |
| Distilled water | qs | 100 |

The emulsion is prepared according to the procedure of Example 1. A composition which is stable for at least 1 month at 45° C. is again obtained.

The disclosure of French priority application 96–12450 filed Oct. 11, 1996 is hereby incorporated by reference into the application.

Obviously, numerous modifications and variations of the present invention are possible in light of the above teachings. It is, therefore, to be understood that within the scope of the appended claims, the invention may be practiced otherwise than as specifically described herein.

What is claimed is:

1. A method of alleviating the symptoms of sensitive skin, comprising:
    applying to the skin a topical composition in the form of an O/W emulsion, comprising at least 2% by weight, relative to the total weight of the composition, of at least one water-soluble metal salt, and from 2–4.5% by weight, relative to the total weight of the composition, of an emulsifying system, excluding compositions comprising 1% by weight of a gelling agent consisting of a combination of a polyacrylamide, $C_{13}$–$C_{14}$ isoparaffin and laureth-7.

2. The method according to claim 1, wherein the composition comprises at least 3% by weight of at least one water-soluble metal salt.

3. The method according to claim 2, wherein the content of said metal salt is at least 5% by weight.

4. The method according to claim 1, wherein the water-soluble metal salts are selected from the group consisting of water-soluble salts of alkali metals, of alkaline earth metals, of transition metals and of metals from Groups 13 and 14 of the Periodic Table of the Elements.

5. The method according to claim 1, wherein the water-soluble metal salts are selected from the group consisting of lithium, strontium, barium, yttrium, neodymium, gadolinium, manganese and zinc salts.

6. The method according to claim 1, wherein the water-soluble metal salts are selected from the group consisting of carbonates, bicarbonates, sulfates, glycerophosphates, borates, chlorides, nitrates, acetates, hydroxides, persulfates, α-hydroxy acid salts, amino acid salts and fatty acid salts.

7. The method according to claim 1, wherein the amount of water-soluble metal salts ranges from 2–20% by weight relative to the total weight of the composition.

8. The method according to claim 1, wherein the emulsifying system consists of at least one fatty acid ester of polyethylene glycol and/or at least one fatty acid ester of a polyoxyethylenated polyol, optionally combined with at least one fatty acid ester of a polyol, which are suitable for the preparation of O/W emulsions.

9. The method according to claim 8, wherein the suitable emulsifying system consists of at least one fatty acid ester of PEG and at least one fatty acid ester of a polyol.

10. The method according to claim 8, wherein the fatty acids are selected from the group consisting of linear or branched, saturated or unsaturated aliphatic acids comprising at least 10 carbon atoms.

11. The method according to claim 8, wherein the fatty acid ester of PEG comprises n PEG units, n being an integer at least equal to 8.

12. The method according to claim 8, wherein the polyoxyethylenated fatty acid esters of a polyol are selected from the group consisting of oxyethylenated sorbitan tristearate containing 20 oxyethylene units, oxyethylenated sorbitan trioleate containing 20 oxyethylene units, oxyethylenated sorbitan monolaurate containing five oxyethylene units, oxyethylenated sorbitan monostearate containing 20 oxyethylene units, oxyethylenated sorbitan monopalmitate containing 20 oxyethylene units and oxyethylenated sorbitan monooleate containing 20 oxyethylene units.

13. The method according to claim 8, wherein the fatty acid ester of a polyol is selected from the group consisting of the mono- or polyesters of the reaction product of a fatty acid and of a polyol, the polyol being selected from the group consisting of $C_3$–$C_6$ polyhydric alcohols comprising 3–6 hydroxyls.

14. The method according to claim 13, wherein the $C_{3-6}$ polyhydric alcohol is selected from $C_5$–$C_6$ sugars of natural or synthetic origin.

15. The method according to claim 14, wherein the fatty acid esters of a sugar are selected from the group consisting of the fatty acid mono- or triesters of sorbitol.

16. The method according to claim 13, wherein the fatty acid esters of glycerol are selected from the group consisting of the fatty acid mono- and diesters of glycerol, and mixtures thereof in all proportions.

17. The method according to claim 8, wherein the fatty acid ester of PEG/fatty acid ester of a polyol weight ratio ranges from 0.2–3.

18. The method according to claim 1, wherein the emulsifying system has an HLB of greater than or equal to 9.

19. The method according to claim 1, wherein the composition comprises at least one neuropeptide antagonist and/or at least one inflammation-mediator antagonist, which are other than water-soluble metal salts.

20. The method according to claim 1, which further comprises active compounds which can induce skin irritation.

21. The method according to claim 1, wherein said sensitive skin is an irritable skin or an intolerant skin.

22. A method of alleviating the symptoms of sensitive skin, comprising:
    applying to the skin a topical composition in the form of an O/W emulsion, comprising at least 2% by weight, relative to the total weight of the composition, of at least one water-soluble carbonate, bicarbonate, sulfate, glycerophosphate, borate, chloride, nitrate, acetate, hydroxide, persulfate, citrate, tartrate or malate, compound of sodium, potassium, an alkaline earth metal, a transition metal, a metal of Groups 13 and 14 of the Periodic Table or a lanthanide element or a water-soluble compound of one of said metals with an amino acid or a fatty acid, and from 2–4.5% by weight, relative to the total weight of the composition, of an emulsifying system, excluding compositions comprising 1% by weight of a gelling agent consisting of a combination of a polyacrylamide, $C_{13}$–$C_{14}$ isoparaffin and laureth-7.

23. A composition in the form of an O/W emulsion, comprising:

a component which alleviates the irritability and intolerance of sensitive skin consisting of at least 2% by weight, relative to the total weight of the composition, of at least one water-soluble carbonate, bicarbonate, sulfate, glycerophosphate, borate, chloride, nitrate, acetate, hydroxide, persulfate, citrate, tartrate or malate, compound of sodium, potassium, an alkaline earth metal, a transition metal, a metal of Groups 13 and 14 of the Periodic Table or a lanthanide element or a water-soluble compound of one of said metals with an amino acid or a fatty acid, and from 2–4.5% by weight, relative to the total weight of the composition, of an emulsifying system, excluding compositions comprising 1% by weight of a gelling agent consisting of a combination of a polyacrylamide, $C_{13}$–$C_{14}$ isoparaffin and laureth-7.

* * * * *